United States Patent
Tio Castro et al.

(10) Patent No.: US 8,912,478 B2
(45) Date of Patent: Dec. 16, 2014

(54) LIGHT SENSOR WITH A PHOTORESISTIVE ELEMENT HAVING A COMB STRUCTURE

(75) Inventors: David Tio Castro, Heverlee (BE);
Aurelie Humbert, Brussels (BE)

(73) Assignee: NXP, B.V., Eindhoven (NL)

( * ) Notice: Subject to any disclaimer, the term of this patent is extended or adjusted under 35 U.S.C. 154(b) by 169 days.

(21) Appl. No.: 13/156,742

(22) Filed: Jun. 9, 2011

(65) Prior Publication Data
US 2011/0303829 A1    Dec. 15, 2011

(30) Foreign Application Priority Data
Jun. 9, 2010 (EP) .................................... 10165448

(51) Int. Cl.
| | | |
|---|---|---|
| H01L 31/00 | (2006.01) | |
| G01J 5/38 | (2006.01) | |
| G01J 1/42 | (2006.01) | |
| G01N 17/04 | (2006.01) | |

(52) U.S. Cl.
CPC .... G01J 5/38 (2013.01); G01J 1/42 (2013.01); G01N 17/043 (2013.01)
USPC ..................................................... 250/214.1

(58) Field of Classification Search
USPC .......... 250/214.1; 257/2, 228, 291; 73/335.05
See application file for complete search history.

(56) References Cited

U.S. PATENT DOCUMENTS

| | | | |
|---|---|---|---|
| 3,415,990 A | 12/1968 | Watson | |
| 6,278,117 B1 * | 8/2001 | Bardash | ................... 250/370.07 |
| 2001/0040631 A1 | 11/2001 | Ewerdmi et al. | |
| 2002/0093657 A1 | 7/2002 | Friberg et al. | |
| 2006/0121678 A1 | 6/2006 | Brask et al. | |
| 2010/0230729 A1 * | 9/2010 | Ellis-Monaghan et al. | .. 257/228 |

FOREIGN PATENT DOCUMENTS

| | | |
|---|---|---|
| CN | 1469993 A | 9/2000 |
| CN | 1363957 A | 8/2002 |
| CN | 101099241 A | 1/2008 |
| EP | 2075549 A1 | 1/2009 |
| GB | 1166397 A | 3/1967 |
| JP | 2009007403 A | 1/2009 |
| WO | 2007/002161 A2 | 1/2007 |

OTHER PUBLICATIONS

Lendlein, "Light-induced shape-memory polymers," Apr. 14, 2005, Nature, vol. 434, pp. 879-882.*
Nicola, S. et al. "Cultivation Management on the Farm Influences Postharvest Quality and Safety", ISHS, International Conf. on Quality Management of Fresh Cut Produce, pp. 273-280 (2007).
Gupta, T. K. "Correlation of the Chemical and Electrical Properties of AZ1350J Photoresist Solution", J. Appl. Phys. 56, pp. 1145-1148 (Aug. 15, 1984).
Extended European Search Report for Patent Appln. No. 10165448.1 (Oct. 8, 2010).

* cited by examiner

*Primary Examiner* — Thanh Luu
*Assistant Examiner* — Renee Naphas

(57) ABSTRACT

The light dose received by perishable goods is an important parameter in determining the lifetime of those goods. A light sensor is described having a photosensitive element which changes its material property according to the light dose received. This change can be detected electrically by electrodes in the light sensor. Because the change in material property is permanent, this removes the need for a memory to store a value representing the light dose received by the light sensor.

15 Claims, 4 Drawing Sheets

LIGHT SENSOR WITH A PHOTORESISTIVE ELEMENT HAVING A COMB STRUCTURE

CROSS-REFERENCE TO RELATED APPLICATIONS

This application claims the priority under 35 U.S.C. §119 of European patent application no. 10165448.1, filed on Jun. 9, 2010, the contents of which are incorporated by reference herein.

BACKGROUND

This invention relates to light sensors.

RFID (Radio Frequency Identification) refers to the use of an electronic device, generally called RFID tag, incorporated into a target (goods or life beings). This device is used to transmit information from the target to a reader using radio frequencies.

RFID tags typically consist of an RFID transmitter for modulating and demodulating a radio-frequency (RF) signal, an RFID antenna for receiving and transmitting the signal, and an integrated circuit for storing and processing information and other specialized functions.

RFID tags can be active, if they contain a power source which allows them to operate independently, or passive, if the power is induced from an external source, typically via the RFID reader itself.

RFID sensors are a particular variation of RFID tags. Typically RFID tags are used for identification purposes. By integrating sensors into the RFID tag, much more functionality becomes available.

In an application of an RFID sensor, the environmental conditions to which a particular product is exposed can be tracked during its lifetime in the supply chain, and then transmitted to an RFID reader. The use of integrated sensors allows the monitoring of environmental conditions to which a perishable product is exposed. With appropriate algorithms, this data can be translated into estimation of remaining lifetime.

In order for an RFID sensor to be economically viable, the price of the sensor must be significantly less than the price of the product to be monitored.

The cost of the global annual waste of perishable products totals approximately US$35 Billion. This includes food, drinks, flowers, pharmaceuticals, vaccines, blood, and chemicals. The cold chain represents the refrigerated and controlled supply chain of these products from production, transportation, and storage to the end-user. By smart tagging of perishable products, a great deal of waste can be avoided. RFID tags on the products and containers include sensors for a number of environmental parameters such as temperature, humidity, O2/CO2 concentration and pH.

The light dose is a very important parameter influencing the quality and lifetime of perishables (see for example, Nicola E. Fontana, Cultivation management on the farm influences postharvest quality and safety, International Conference on Quality Management of Fresh Cut Produce, 2007). A light sensor integrated into an RFID sensor monitors the light dose certain goods have received. This information must be stored until an external RFID readout occurs. In order to store the sensor readout, a memory is required. However the use of a memory has some disadvantages; for example a power supply is required to program or keep the data in the memory and furthermore the circuit is more complex, resulting in a more costly sensor.

Therefore, there is a need to develop a cheaper light sensor.

SUMMARY OF INVENTION

According to a first aspect of the invention, there is provided a light sensor comprising: a photosensitive element configured to react to exposure to light, first and second electrodes for measuring a value indicating a material property of the photosensitive element, wherein the value is representative of the light dose received by the photosensitive element.

The reaction of the photosensitive element to light alters a material property of the photosensitive element according to the light dose received. The change in the material property is permanent, permanent meaning that the altered property will remain in the new state for a duration which is long enough to allow readout. The change is detected by the detection of the changes in an electrical property of the photosensitive element between the first and second electrodes, which is associated to physical or mechanical changes in the photosensitive element.

The altered material property means that the photosensitive element acts as a memory, storing the amount of light received by the light sensor. This means that there is no requirement for a conventional memory or a power supply.

According to an embodiment of the invention, the light sensitive element comprises a polymer. Using a polymer allows the sensor to be made using a standard CMOS process.

In a further embodiment the polymer is a photoresist, for example OiR 620-09, OiR 620-10, OiR 620M-10, M91Y-450, JSR M91Y DUV or TOK 3150 MUV, I-AC77-R168-330 which are used in CMOS processes.

In an embodiment of the invention, the photosensitive element is configured to reduce in thickness when exposed to light. The reduced amount can be detected electrically by, for example, a change in resistance or capacitance between the first and second electrodes.

In a further embodiment of the invention, the light sensor is configured such that the dielectric constant of the photosensitive element changes as a function of the light dose received by the photosensitive element up to a maximum dose. The change in dielectric constant can be detected electrically by, for example, measuring the capacitance between the first and second electrodes. Once the maximum light dose has been received the sensor saturates.

BRIEF DESCRIPTION OF DRAWINGS

Further embodiments of the invention will now be described by way of example only with reference to the accompanying drawings in which:

FIG. 1 shows a cross-section of a light sensor 10 according to an embodiment of the invention. A first electrode 12 and a second electrode 14 can be deposited on a substrate 16. A photosensitive element 18, which can be a polymer, is deposited between the first electrode 12 and the second electrode 14. In operation, an electrical measurement can be taken between the first electrode 12 and the second electrode 14, which indicates material property of the photosensitive element 18.

When the photosensitive element is exposed to light, the material property of the photosensitive element 18 can change. This change can be caused by the interaction of light causing at least some of the chemical bonds in the material to break. This change can be detected by making a second electrical measurement between the first electrode 12 and the second electrode 14 of the light sensor 10. The difference between the first value measured before the photosensitive element 18 is exposed to light and the second measurement taken after the photosensitive element 18 is exposed to light is thus representative of the light dose received by the light sensor 10.

The photosensitive element 18 can be made from any material where the property changes as a function of light dose that can be detected electrically, and the change last for a duration long enough, such that the change in value before exposure to light and after exposure to light can be measured. Examples of such material are a polymer such as photo resist, whose properties, for example, dielectric constant and resistivity can change when the material is exposed to light. Once the light dose has exceeded a maximum value the photosensitive element can saturate and consequently no further change can be measured.

The first and second measurements made can be, for example, a measurement of the value of resistance or capacitance between the first electrode 12 and the second electrode 14.

First electrode 12 and second electrode 14 can be formed from any suitable conductive material such as metal e.g. aluminium or copper, or an alloy. Substrate 16 can be formed from any material suitable for depositing electrodes and polymers. Substrate 16 can, for example, be formed from silicon or layers deposited on top of silicon such as layers forming transistors, metallisation layers dielectric layer or any other layers commonly used in the formation of integrated circuits. The first electrode 12, second electrode 14, and photosensitive element 18, can be formed using standard CMOS processing techniques such as evaporation deposition and spluttering.

The dimensions of the first electrode 12, second electrode 14 and the spacing between the electrodes can be determined by the CMOS standard processing rules. Example ranges for a CMOS14 process are for a first electrode 12 having a width between 50 nm and 10 um a second electrode 14 having a width between 50 nm and 10 um, and the spacing between electrodes being in the range of 50 nm and 10 um.

Figure 1:
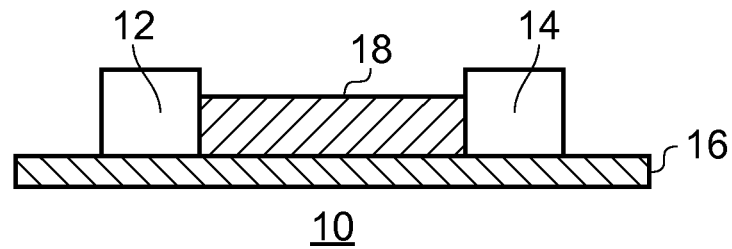
FIG. 1 shows a light sensor according to a first embodiment of the invention.
Figure 2A:
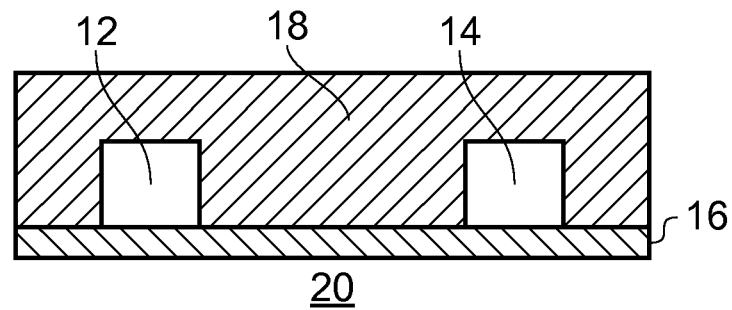
FIG. 2 illustrates a light sensor according to a further embodiment of the invention.
Figure 2B:
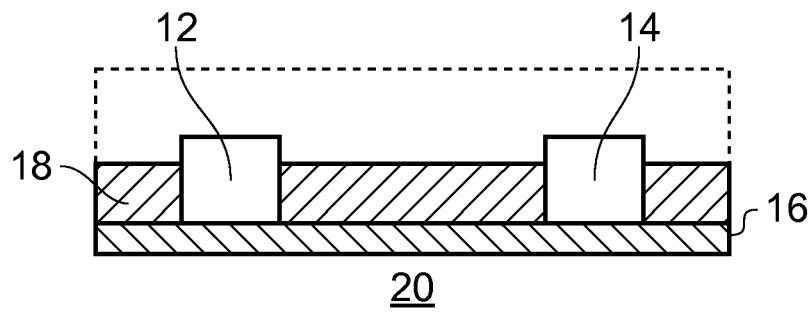

FIGS. 2A and 2B show a cross section of a light sensor 20 according to a further embodiment of the invention. A first electrode 12 and a second electrode 14 are deposited on a substrate 16. A photosensitive layer is deposited on top of the first and second electrodes to form a photo sensitive element 18. This layer can also be adjacent to the substrate 16. In operation, before the light sensor 20 is exposed to a light source, an electrical measurement is taken between the first electrode 12 and the second electrode 14, which represents a material property of the photosensitive element 18. When the light sensor 20 is exposed to light, the light source can cause at least some of the chemical bonds in the photosensitive element 18 to break. This can result in the photosensitive element 18 having a reduced thickness, which has the effect of altering the electrical property of the photosensitive element 18, because the reduced thickness can result in a change in resistance or capacitance. This change in resistance or capacitance can be detected by a further measurement between the first electrode 12 and the second electrode 14.

The difference in the electrical measurement taken between the readings before the light sensor 20 is exposed to a light source, and the reading taken after the photosensitive element is exposed to a light source is representative of the light dose received by the light sensor 20. A measured change of capacitance can be, for example, several pF. A measured change in resistance can be, for example, an increase or decrease of 10% of the value of the resistance before exposure to a light source.

Figure 3A:
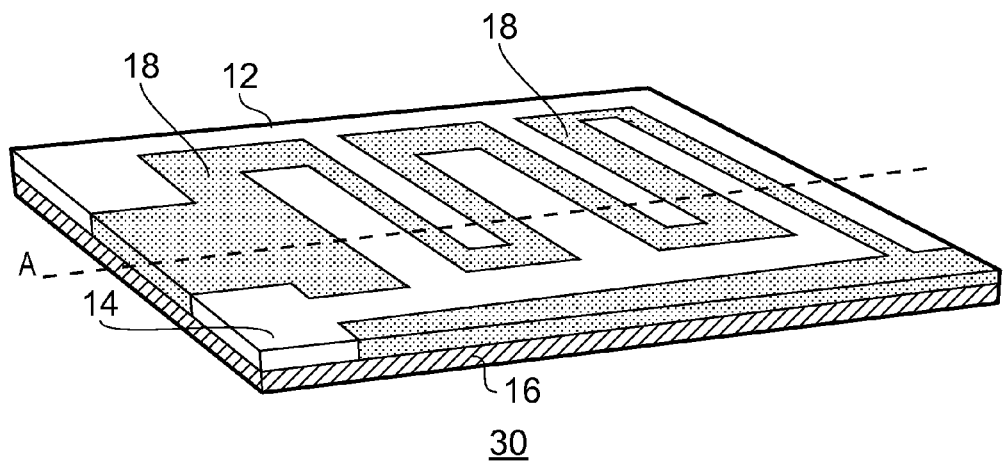
FIG. 3A show a light sensor according to another embodiment of the invention.
Figure 3B:
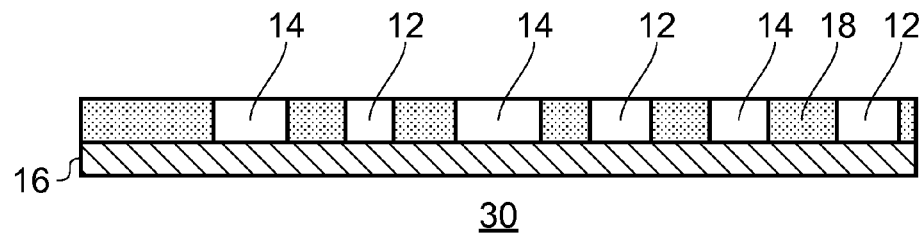
FIG. 3B shows a cross section view of the light sensor of FIG. 3A.

FIGS. 3A and 3B show a light sensor 30 according to a further embodiment of the invention. FIG. 3 illustrates a first electrode 12 and second electrode 14 deposited on a substrate 16. The first electrode 12 and the second electrode 14 are formed from a comb structure with the teeth of the comb being interleaved between one another. This structure can also be referred to as a meandered comb structure. A layer of photosensitive material is deposited between the first electrode 12 and the second electrode 14. This layer of photosensitive material forms a photosensitive element 18. FIG. 3B shows a cross-section of the embodiment of the light sensor 30 shown in FIG. 3A.

The light sensor can be operated by making a first measurement between the first electrode and the second electrode indicating a material property of the photosensitive element 18 before it has been exposed to a light source. Once the photosensitive element 18 has been exposed to light the material property of the photosensitive element 18 can change. This material property can be for example the dielectric constant of the material, the resistivity of the material, or the thickness of the material if the incidence of light on the material causes the thickness of the material to reduce. A second measurement after the exposure of the light sensor 30 to a light dose can then be made.

This measurement can be for example the change in value of the resistance or the capacitance between the first electrode 12 and the second electrode 14. The difference in the value measured before the light sensor 30 was exposed to light and the light sensor 30 after it was exposed to light gives a measurement representative of the amount of light or the light dose received by the light sensor 30.

In a further embodiment, the light sensor 30 can be sensitive to a specific wavelength or wavelength of light, so the measurements taken before and after exposure to light can indicate the light dose of a certain wavelength or a range of wavelengths received by the light sensor. An example of a material for use in photosensitive element 18 is OiR 620-09, sensitive to wavelengths in the range of 360 nm to 390 nm. Another example of a material for use in photosensitive element 18 is M91Y-450 sensitive to wavelengths in the range of 230 nm to 260 nm with a peak sensitivity to light of wavelength 248 nm. A further example of a material for use in photosensitive element 18 is I-AC77-R168-330 which is sensitive to wavelengths in the range of 190 nm to 205 nm, with peak sensitivity to light of wavelength 193 nm. Other embodiments can have a material for use in the photosensitive element 18 that is sensitive to light in the visible spectrum. Further embodiments can have materials for use in the photosensitive element 18 that is sensitive to light in the solar radiation spectrum.

FIGS. 4A, 4B, 4C, 4D illustrate the steps in manufacturing an example of the light sensor 40 in cross-section, according to a further embodiment of the invention using a standard CMOS process such as CMOS 14.

Figure 4A:
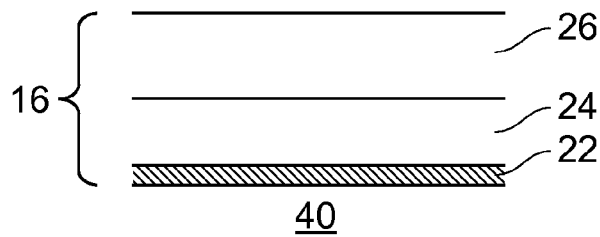
FIG. 4A to 4D illustrate the steps in manufacturing a light sensor according to a further embodiment of the invention.

FIG. 4A shows a layer of silicon nitride 22, on which a layer of silicon 24 can be deposited. Alternatively, the SiN layer 22 can be formed as wafer bottom isolation, under the layer of silicon 24. A layer of HDP oxide 26 can be deposited on the layer of silicon 24. The thickness of the HDP oxide layer is in the range of 600 nm to a 1000 nm. The silicon nitride layer 22 and silicon layer 24 form a silicon-on-insulator structure. The silicon nitride layer 22, silicon layer 24 and HDP oxide layer 26 can form substrate 16.

Figure 4B:
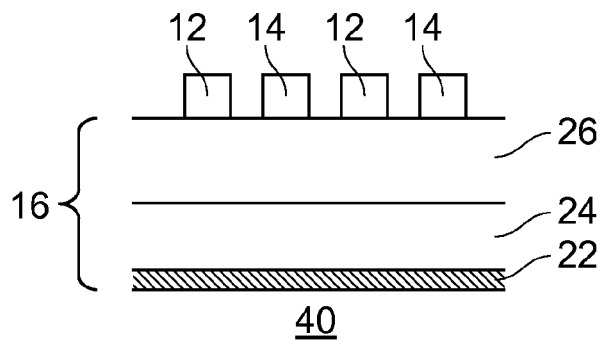

FIG. 4B shows the formation of the first electrode 12 and second electrode 14. This can be done by patterning a metal layer which can be made from any suitable conductive material, for example copper or aluminium, to form a first electrode 12 and a second electrode 14. The first electrode 12 and second electrode 14 can have a meandered comb construction.

Further embodiments with alternative structures for the first electrode 12 and the second electrode 14 will be apparent to the person skilled in the art.

The spacing between the first electrode 12 and the second electrode 14 is typically in the range of 50 nm to 10 um.

Figure 4C:
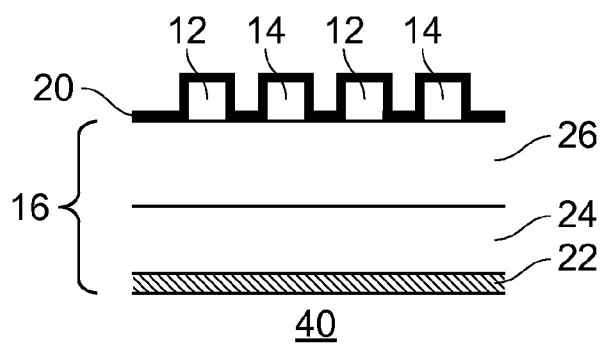

FIG. 4C shows a dielectric layer or capping layer 20 is deposited on the first electrode 12 and the second electrode 14. This dielectric layer 20 can be a passivation layer.

Figure 4D:
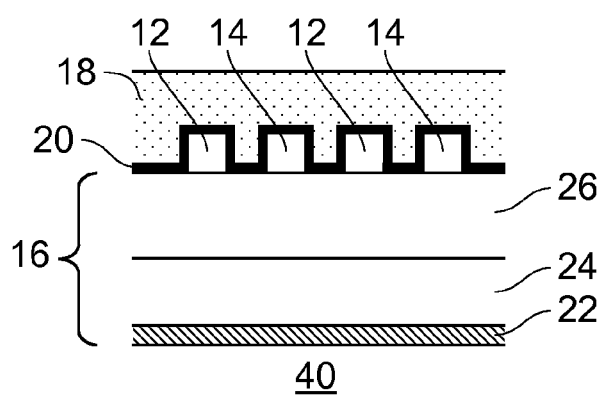

A layer of photosensitive material is deposited above and around and between the first electrode 12 and the second electrode 14 as shown in FIG. 4D. This layer forms a photosensitive element 18. The thickness of the photosensitive element 18 is in the range of 2 um to 20 um.

Figure 5A:
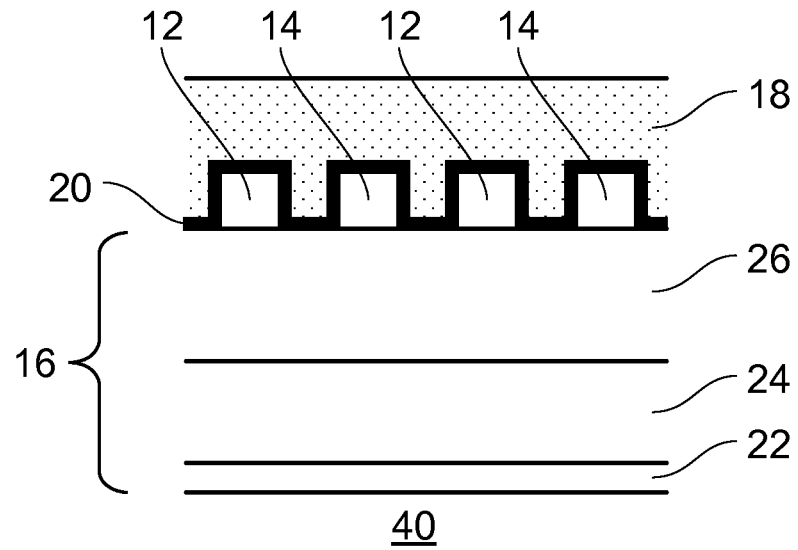
FIGS. 5A and 5B shows the embodiment of FIG. 4A to 4D before and after use to monitor light dose.

The layers used to form the light sensor 40 shown in FIGS. 4A to 4D are formed using standard CMOS processing techniques such as evaporation deposition and splluttering. The resulting light sensor 40 formed by the processing steps as shown in FIGS. 4A to 4D is shown in FIG. 5A.

A layer of silicon 24 can be formed on a layer of silicon nitride 22. Alternatively, the SiN layer 22 can be formed as wafer bottom isolation, under the layer of silicon 24. A dielectric layer is formed by deposition of an oxide layer 26 on silicon layer 24. Silicon nitride layer 22 and silicon layer 24 form a silicon-on-insulator. Silicon nitride layer 22, silicon layer 24 and oxide layer 26 can form a substrate 16. First electrode 12 and second electrode 14 are formed on the oxide layer 26. Further dielectric layer 20 is formed on the first electrode 12 and the second electrode 14. A layer of photosensitive material which can be a polymer is formed on the further dielectric layer 20 and in between the first electrode 12 and the second electrode14. The photosensitive layer forms a photosensitive element 18.

In operation light sensor 40 works as follows. A first measurement is taken before the light sensor 40 is exposed to light having wavelength or range of wavelengths to which the photosensitive element 18 is sensitive. This reading is an electrical measurement and can be, for example the resistance or the capacitance between the first electrode 12 and the second electrode 14.

Figure 5B:
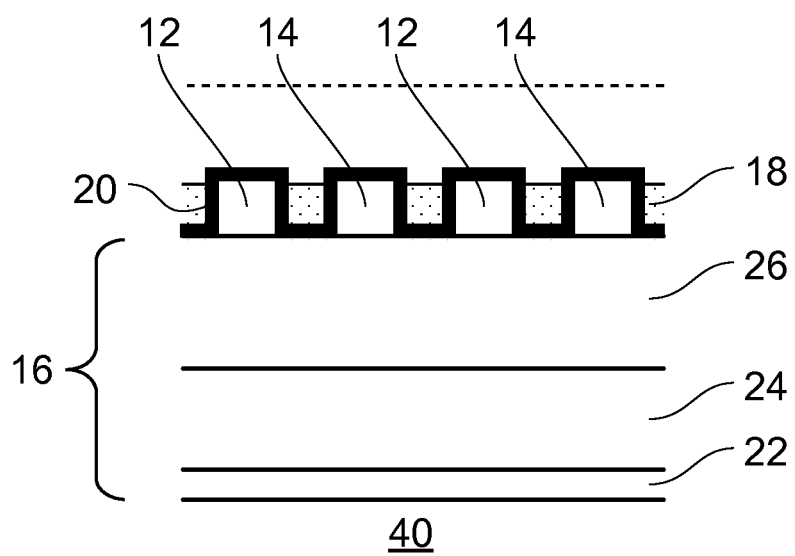

FIG. 5B illustrates the effect of light incident on the light sensor 40. Exposure to a light dose of the layer of photosensitive material 18 can cause at least some of the chemical bonds in the material to break. This can result in a reduced thickness of the photosensitive element 18. This change can be detected by a further electrical measurement between the first electrode 12 and the second electrode 14. The difference in value between the first measurement and the second measurement corresponds to the amount of light or the light dose received by the light sensor 40. This can be a measurement of the total amount of light incident on the light sensor 40 of a specific wave length or range of wave lengths.

In an alternative embodiment the change in material property of the light sensor 40 can be a change in the dielectric constant of the material of the photosensitive element 18 once the photosensitive element 18 has been exposed to light. In a further embodiment the change in material property of the photosensitive element 18 can be a change in the resistivity of the material of the photosensitive element 18, once the photosensitive element 18 is exposed to light. The change in material property of the light sensor 40 corresponds to the light dose received by the sensor 40.

In an alternative embodiment, changes in a combination of dielectric constant, resistivity and the thickness of the photosensitive element 18 can be detected by measuring an electrical change between first electrode 12 and second electrode 14.

It is clear to the skilled person that from the invention as disclosed herein, further embodiments are possible. All embodiments described herein can be formed using standard CMOS processing techniques. A substrate can be silicon or other suitable material. A substrate can also be layers above a silicon layer used to form integrated circuits. The photosensitive element 18 can be protected from being prematurely exposed to light during processing by coating the photosensitive element 18 with an adhesive opaque material which can be subsequently removed. Alternatively, for some embodiments, the processing can be done in an area lit by a light of wavelength to which the photosensitive element 18 is not sensitive. The light sensor can have an adhesive label to cover the photosensitive element 18 which can be peeled off before use. Further embodiments of the light sensor can have an adhesive label which filters the light in the light sensitive range of the sensor only. It is also possible to protect the sensor by freezing the sensor until used.

Further embodiments can integrate the light sensor with other integrated circuits and with specific types of integrated circuits such as RFID tags Other embodiments of the light sensor can be integrated into RFID sensors, used for example supply chain management and for tagging perishable goods. Further embodiments of the light sensor can include for example CMOS integrated sensors and integrated sensor arrays.

The materials used for the photosensitive element can be materials that are commonly used in CMOS processing technology, such as photo resist materials. The change caused by the exposure to light in photo resist materials can be permanent. However, any material whereby exposure to light causes a change in the material properties, and where the change in material property can be detected electrically, can be used in embodiments of the invention. The change has to be stable until the next measurement cycle. The interval between measurement cycles can be a few seconds, several days or several months.

For some embodiments described herein, the final value of capacitance and resistance can also be dependent on the wavelength of light incident on the sensor, so embodiments of the invention can also be used as a wavelength detector.

Application of the use of such light sensors according to embodiments of the invention which are integrated into RFID sensors can be in perishables monitoring, raw materials tracking, supply chain management, use in intelligent labelling, and use in abuse control labelling.

There is described herein a light sensor (30) having a photosensitive element (18) which changes its material property according to the light dose received. This change can be detected electrically by electrodes (12, 14) in the light sensor. Because the change in material property is permanent, this removes the need for a memory to store a value representing the light dose received by the light sensor.

The invention claimed is:

1. A light sensor comprising:
   a photosensitive element configured to react to exposure to light, resulting in a change in a material property of the photosensitive element;
   first and second electrodes configured and arranged in a comb structure for measuring a value indicating the material property of the photosensitive element, wherein the value is representative of a light dose received by the photosensitive element and is capacitance of the photosensitive element, and the photosensitive element comprises a photoresist polymer.

2. The light sensor according to claim 1, wherein the photosensitive element is configured and arranged to reduce in thickness when exposed to the light.

3. The light sensor according to claim 1, wherein the light sensor is configured and arranged such that a dielectric constant of the photosensitive element changes as a function of the light dose received by the photosensitive element.

4. The light sensor according to claim 1, wherein the light sensor is configured and arranged such that resistivity of the photosensitive element changes as a function of the light dose received by the photosensitive element.

5. The light sensor according to claim 1, the light sensor further comprising:
   a substrate,
   a dielectric layer, wherein the first and second electrodes are adjacent to the substrate, the dielectric layer is adjacent to the first and second electrodes, and the photosensitive element is adjacent to the dielectric layer.

6. The light sensor of claim 5, wherein the substrate comprises silicon-on-insulator and a further dielectric layer on the silicon-on-insulator.

7. A light wavelength detector comprising the light sensor according to claim 1.

8. An RFID sensor comprising the light sensor of claim 1.

9. A system for monitoring perishable goods comprising the RFID sensor of claim 8.

10. A label for packaging comprising the RFID sensor of claim 8.

11. A CMOS sensor array comprising the light sensor of claim 1.

12. A CMOS integrated circuit comprising the light sensor of claim 1.

13. The light sensor according to claim 1, wherein the comb structure is a meandered comb structure.

14. The light sensor according to claim 1, wherein teeth of the comb structure are interleaved.

15. The light sensor according to claim 1, wherein a layer of photosensitive material is deposited between the first electrode and the second electrode.

* * * * *